(12) United States Patent
Schulhoff et al.

(10) Patent No.: US 7,183,246 B2
(45) Date of Patent: Feb. 27, 2007

(54) CLEANING/DISINFECTANT COMPOSITION TO CLEAN SURFACES

(75) Inventors: Jeffrey Schulhoff, Oklahoma City, OK (US); Christian Schaal, Nettetal (DE)

(73) Assignee: Floran Technologies Inc., Oklahoma City, OK (US)

( * ) Notice: Subject to any disclaimer, the term of this patent is extended or adjusted under 35 U.S.C. 154(b) by 0 days.

(21) Appl. No.: 10/012,003

(22) Filed: Oct. 29, 2001

(65) Prior Publication Data
US 2002/0094941 A1 Jul. 18, 2002

Related U.S. Application Data

(60) Division of application No. 09/584,892, filed on Jun. 1, 2000, now Pat. No. 6,309,470, which is a continuation-in-part of application No. 09/324,383, filed on Jun. 2, 1999, now Pat. No. 6,346,217.

(51) Int. Cl.
*C11D 17/00* (2006.01)

(52) U.S. Cl. ............... 510/245; 510/247; 510/253; 510/254; 510/255; 134/2; 134/3; 134/22.1; 134/22.11; 134/26; 134/28; 134/36; 252/186.1

(58) Field of Classification Search ............... 510/119, 510/245, 246, 247; 134/26
See application file for complete search history.

(56) References Cited

U.S. PATENT DOCUMENTS

| 4,199,469 A | * | 4/1980 | Walzer ............... 252/146 |
| 5,750,733 A | * | 5/1998 | Vermeer et al. ........ 549/346 |
| 6,106,774 A | * | 8/2000 | Monticello et al. ....... 422/28 |

* cited by examiner

*Primary Examiner*—Necholus Ogden
(74) *Attorney, Agent, or Firm*—Borden Ladner Gervais LLP

(57) ABSTRACT

A composition and method for cleaning surfaces having deposits, such as drink water tanks, supply water wells, water filter systems, and distributor water lines. The composition contains in combination a cleaning solution and a disinfectant, such as hydrogen peroxide or peracidic acid. The cleaning solution can includes hydrochloric acid and/or phosphoric acid in combination with inhibitors, dyes and water. The composition is applied to deposits which have formed on these surfaces.

11 Claims, No Drawings

CLEANING/DISINFECTANT COMPOSITION TO CLEAN SURFACES

REFERENCE TO PENDING APPLICATIONS

This application is a divisional application of U.S. patent application Ser. No. 09/584,892 filed on Jun. 1, 2000 entitled A COMPOSITION AND METHOD FOR CLEANING SURFACES (will be U.S. Pat. No. 6,309,470 on Oct. 30, 2001) which is a continuation-in-part of U.S. patent application Ser. No. 09/324,383 filed on Jun. 2, 1999 now U.S. Pat. No. 6,346,217 entitled A COMPOSITION AND METHOD FOR CLEANING DRINK WATER TANKS (allowed on Sep. 10, 2001 and issue fee will be paid).

REFERENCE TO MICROFICHE APPENDIX

This application is not referenced in any microfiche appendix.

BACKGROUND OF THE INVENTION

This invention relates generally to the cleaning of surfaces having deposits and more particularly, to the removal of particular types of deposits formed along these surfaces. Such surfaces are located along internal surfaces of drink water tanks, supply water wells, water filter systems, and distributor water lines.

Typically these surfaces are constantly being exposed to water and air. For example, the water level of a drink water tank rises and falls with demand. This constant change between water exposure and air exposure cause a biological film, such as algae and microorganisms, along with incrustations such as calcium, iron and manganese to form deposits along these surfaces.

Cleaning these deposits from these surfaces has been the subject of a number of prior art compositions. U.S. Pat. No. 4,199,469 issued to Waltzer on Apr. 22, 1980 discloses a composition and method for cleaning drink water tanks. This composition utilizes a group of acids (ascorbic, formic, phosphoric, citric and hydrochloric).

Once the surfaces have been cleaned by a cleaning composition, a disinfectant is normally applied. This additional process adds time and resources to the overall cleaning process. Given the number of constituents the composition is complicated and confusing. Therefore, there exists a need for a more simple composition in order to clean surfaces having deposits contained thereon.

BRIEF SUMMARY OF THE INVENTION

This invention relates generally to the cleaning of surfaces having deposits and more particularly, to the removal of particular types of deposits formed along these surfaces. Such surfaces can be located along internal surfaces of drink water tanks, supply water wells, water filter systems, and distributor water lines.

The present invention is directed, generally, to a composition for such surfaces. The composition includes in combination a cleaning solution portion and a disinfectant portion.

The cleaning solution portion generally includes hydrochloric acid and/or phosphoric acid in combination with inhibitors, dyes and water. The disinfectant is a standard disinfectant, such as but not limited to hydrogen peroxide or peracidic acid.

The composition is applied to the surfaces having deposits of biological film, such as but not limited to algae and microorganisms and/or incrustations such as but not limited to calcium, iron and manganese thereon. The solution loosens the adhesion between the deposits and the surface at which time the composition and deposits are rinsed away. Further, the biological film is reliably eliminated.

It is a primary object of the invention to provide a composition and method for cleaning surfaces that avoids the problems mentioned above.

Another object of the invention is to provide a solution for cleaning and disinfecting such surfaces.

Other objects and further scope of the applicability of the present invention will become apparent from the detailed description to follow wherein like parts are designated by like reference numerals.

DETAILED DESCRIPTION OF THE PREFERRED EMBODIMENTS

This invention relates generally to the cleaning of surfaces having deposits and more particularly, to the removal of particular types of deposits formed along these surfaces. Such surfaces are located along internal surfaces of drink water tanks, supply water wells, water filter systems, and distributor water lines.

The present invention is directed, generally, to a composition for cleaning such surfaces. The composition includes in combination a cleaning solution portion (90–99.9% by volume) and a disinfectant portion (0.1–10% by volume). The composition is applied to drink water tank surfaces which have deposits formed thereon.

The cleaning solution portion generally includes hydrochloric acid and/or phosphoric acid in combination with inhibitors, dyes and water. The disinfectant is a standard disinfectant, such as but not limited to hydrogen peroxide or peracidic acid.

The preferred embodiment of the present invention is directed toward the cleaning of surfaces specifically for the removal of deposits which have formed thereon and providing a disinfectant in combination.

With respect to the cleaning solution portion, one basic formula is:

| Ingredients | Weight Percentage (Preferred) |
| --- | --- |
| Sulfamic | 0–20%/2.0% |
| Citric Acid | 0–10%/10.0% |
| Glycolic Acid | 0–15%/14.6% |
| Phosphoric Acid | 0–13%/12.9% |
| Hydrochloric Acid | 0–10%/10.0% |
| Dyes | 0–0.01%/0.009% |
| Water | Balance |

| Ingredients | Weight Percentage (Range/Preferred) |
| --- | --- |
| Hydrochloric Acid | 0–20%/9.0% |
| Citric Acid | 0–1.5%/0.4% |
| Glycolic Acid | 0–15%/14.6% |
| Phosphoric Acid | 0–4%/2.0% |
| Triethylene glycol | 0–1.0%/0.50% |
| Water | Balance |

-continued

II.

| Ingredients | Weight Percentage (Range) |
| --- | --- |
| Sulfamic Acid | 0–20 % |
| Hydrochloric Acid | 0–20.0% |
| Phosphoric Acid | 0–20.0% |
| Inhibitor | 0–1.0% |
| Isopropanol | 0–1.0% |
| Water | Balance |

III.

| Ingredients | Weight Percentage (Range) |
| --- | --- |
| Phosphoric Acid | 5.0–20.0% |
| Inhibitor | 0–1.0% |
| Isopropanol | 0–1.0% |
| Water | Balance |

A disinfectant portion in added to cleaning solution in order to provide a disinfecting capability. The disinfectant portion is a standard disinfectant, such as but not limited to hydrogen peroxide or peracidic acid. The range of the disinfectant portion is 0.1 to 10.0% by volume of the entire composition.

The composition of the preferred embodiment of the present invention is applied to the surface where deposits have formed. These deposits comprise the combination of a biological film, such as algae and microorganisms, with sediments, such as calcium, iron and/or manganese. The composition of the preferred embodiment loosens the adhesive bond between the deposits and the wall surface allowing for the removal thereof. The composition is then rinsed away along with the loosened deposits as well as any remaining biological film.

It is to be understood that the above description is illustrative only and not limiting of the disclosed invention.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed:

1. A composition for removing deposits from surfaces of drink water installations, consisting of
   a cleaning solution portion;
   a disinfectant solution portion, said disinfectant portion being selected from the group consisting of peracetic acid and hydrogen peroxide, wherein the cleaning solution portion includes sulfamic acid 2–20%, phosphoric acid 2–20% and an acid component selected from the group of, citric acid, glycolic acid and combinations thereof; and optionally including in said cleaning solution portion inhibitors, dyes, triethylene glycol, isopropanol and water.

2. The composition of claim 1, wherein said cleaning solution portion is in a range of 90 to 99.9% by volume of the total volume of the composition and said disinfectant portion is in a range of 0.1 to 10.0% by volume of the total volume of the composition.

3. The composition of claim 1, wherein said cleaning solution portion is in a range of 90 to 99.9% by volume of the total volume of the composition and said disinfectant portion is in a range of 0.1 to 10.0% by volume of the total volume of the composition.

4. The composition of claim 1, wherein said cleaning solution portion is consisting of the following by volume:
   sulfamic acid, 2–20%;
   citric acid, 0–10%;
   glycolic acid, 0–15%;
   phosphoric acid, 2–13%.

5. The composition of claim 4, wherein said cleaning solution portion is in a range of 90 to 99.9% by volume of the total volume of the composition and said disinfectant portion is in a range of 0.1 to 10.0% by volume of the total volume of the composition.

6. The composition of claim 1, wherein said cleaning solution portion is consisting of the following by volume:
   sulfamic acid, 2–20%;
   citric acid, 0–1.5%;
   glcolic acid, 0–15%;
   phosphoric acid, 2–4%.

7. The composition of claim 6, wherein said cleaning solution portion is in a range of 90 to 99.9% by volume of the total volume of the composition and said disinfectant portion is in a range of 0.1 to 10.0% by volume of the total volume of the composition.

8. The composition of claim 1, wherein said cleaning solution portion is consisting of the following by volume:
   sulfamic acid, 2–20%;
   phosphoric acid, 2–4%.

9. The composition of claim 8, wherein said cleaning solution portion is in a range of 90 to 99.9% by volume of the total volume of the composition and said disinfectant portion is in a range of 0.1 to 10.0% by volume of the total volume of the composition.

10. The composition of claim 1, wherein said cleaning solution portion is consisting of the following by volume:
    sulfamic acid 2–20%;
    phosphoric acid, 2–20%.

11. The composition of claim 10, wherein said cleaning solution portion is in a range of 90 to 99.9% by volume of the total volume of the composition and said disinfectant portion is in a range of 0.1 to 10.0% by volume of the total volume of the composition.

* * * * *